(12) United States Patent
Broncano Atencia et al.

(10) Patent No.: US 8,603,398 B2
(45) Date of Patent: Dec. 10, 2013

(54) FRAGRANCE DELIVERY SYSTEM

(75) Inventors: Toni Broncano Atencia, Barcelona (ES); Silvia Sorribes, Barcelona (ES); Francisco Güell, Barcelona (ES)

(73) Assignee: The Procter & Gamble Company, Cincinnati, OH (US)

(*) Notice: Subject to any disclaimer, the term of this patent is extended or adjusted under 35 U.S.C. 154(b) by 616 days.

(21) Appl. No.: 12/095,727

(22) PCT Filed: Dec. 1, 2006

(86) PCT No.: PCT/NL2006/000602
§ 371 (c)(1), (2), (4) Date: Jul. 16, 2009

(87) PCT Pub. No.: WO2007/064197
PCT Pub. Date: Jun. 7, 2007

(65) Prior Publication Data
US 2010/0221143 A1    Sep. 2, 2010

Related U.S. Application Data

(60) Provisional application No. 60/741,062, filed on Dec. 1, 2005.

(30) Foreign Application Priority Data

Dec. 1, 2005  (NL) ...................................... 1030571
Dec. 1, 2005  (WO) ................ PCT/NL2005/000823

(51) Int. Cl.
*A62B 7/08*     (2006.01)
*A61L 9/00*     (2006.01)

(52) U.S. Cl.
USPC ................ 422/125; 422/120; 422/123; 422/5

(58) Field of Classification Search
USPC ...................................... 422/120, 123, 125, 5
See application file for complete search history.

(56) References Cited

U.S. PATENT DOCUMENTS 5,011,632 A    4/1991  Yano et al.
5,772,074 A *  6/1998  Dial et al. .......................... 222/1

(Continued)

FOREIGN PATENT DOCUMENTS

EP    1 543 844 A2    6/2005
GB    2 347 860       9/2000

(Continued)

OTHER PUBLICATIONS

International Search Report for International Application No. PCT/NL2006/000604; mailed Apr. 24, 2007; 3 pages.

(Continued)

*Primary Examiner* — Regina M Yoo
(74) *Attorney, Agent, or Firm* — Amy I Ahn-Roll (57) ABSTRACT

The invention provides a fragrance delivery system comprising: a control unit for controlling a release mechanism to release at least one selected fragrance, said control unit comprising a selection unit for selecting said selected fragrance from at least two fragrances and controlling said release mechanism to release said selected fragrance, and a switching element for switching said release mechanism between an first state and an second state or vice versa, in which first state said release mechanism releases said selected fragrance at a higher rate than in said second state. The invention further provides a kit of parts comprising said device and a at least two fragrance reservoirs filled with a fragrance chemical. In addition, the invention relates to the use of a control unit for controlling a release mechanism to release a selected one of at least two fragrances in a fragrance delivery system, which control unit comprises a selection unit for selecting said selected fragrance and controlling said release mechanism to release said selected fragrance, and a switching element for switching said release mechanism between an active state and an inactive state or vice versa, and to the use of the present fragrance delivery system to deliver a fragrance to a space which is at least periodically occupied by an individual.

11 Claims, 6 Drawing Sheets

(56) References Cited

U.S. PATENT DOCUMENTS

| | | |
|---|---|---|
| 6,790,408 B2 | 9/2004 | Whitby et al. |
| 7,621,511 B2 | 11/2009 | Hayes-Pankhurst et al. |
| 8,016,207 B2 | 9/2011 | Kvietok et al. |
| 8,153,684 B2 | 4/2012 | Lephart et al. |
| 8,349,251 B2 | 1/2013 | Woo et al. |
| 2002/0159916 A1 | 10/2002 | Whitby et al. |
| 2004/0007787 A1 | 1/2004 | Kvietok et al. |
| 2004/0028551 A1 | 2/2004 | Kvietok et al. |
| 2004/0033067 A1 | 2/2004 | He et al. |
| 2004/0238976 A1 | 12/2004 | Johns |
| 2005/0028819 A1* | 2/2005 | Manne .................... 128/204.11 |
| 2005/0094988 A1 | 5/2005 | Yip et al. |
| 2005/0147523 A1 | 7/2005 | Laudamiel-Pellet et al. |

FOREIGN PATENT DOCUMENTS

| | | |
|---|---|---|
| JP | H02-126648 U | 5/1990 |
| JP | 09201155 | 8/1997 |
| JP | 11 278048 | 10/1999 |
| WO | WO 2004/043502 A1 | 5/2004 |

OTHER PUBLICATIONS

International Search Report for International Application No. PCT/NL2005/000825; mailed Aug. 16, 2006; 3 pages.

International Search Report for International Application No. PCT/NL2006/000602; mailed Mar. 23, 2007; 3 pages.

International Search Report for International Application No. PCT/NL2005/000823; mailed Jul. 24, 2006; 3 pages.

* cited by examiner

FRAGRANCE DELIVERY SYSTEM

CROSS-REFERENCE TO RELATED APPLICATIONS

The present application claims priority as a national stage application of International Patent Application Serial No. PCT/NL2006/000602 filed on Dec. 1, 2006, which claims priority to (a) The Netherlands Application Serial No. NL1030571 filed on Dec. 1, 2005; (b) International Patent Application Serial No. PCT/NL2005/000823 filed on Dec. 1, 2005; and (c) U.S. Provisional Application No. 60/741,062 filed on Dec. 1, 2005—all of which are hereby incorporated herein by reference in their entireties

BACKGROUND

The present invention relates to a fragrance delivery system, and a kit of parts comprising said device and at least two fragrance reservoirs filled with a fragrance substance.

Fragrance dispersion systems are as such known in the art. Many of such systems are directed to the prevention of the habituation of a fragrance composition. The problem encountered in terms of fragrance habituation is that a person in a particular space will become accustomed to a particular fragrance after a period of time.

Whereas many known systems apply just one single fragrance, recently fragrance delivery systems have been developed that contain two fragrances which are delivered in an alternating manner, one after the other. Such delivery systems have, however, various drawbacks. They deal not in an effective manner with the problem of fragrance habituation, since the first fragrance is automatically followed by the second fragrance at a same intensity.

SUMMARY

Object of the present invention is to provide a fragrance delivery systems which deals with the problem of fragrance habituation in an effective manner, whereas at the same time it provides flexibility in the sense that the fragrance intensity may be adjusted to meet more appropriately the size of the space to which the fragrance is to be delivered.

Surprisingly, it has been found that these objects may be realised when use is made of a fragrance delivery system which allows each of the fragrances to be released periodically.

Accordingly, the present invention relates to a fragrance delivery system comprising:
a control unit for controlling a release mechanism to release at least one selected fragrance, said control unit comprising a selection unit for selecting said selected fragrance from at least two fragrances and controlling said release mechanism to release said selected fragrance, and a switching element for switching said release mechanism between an first state and an second state or vice versa, in which first state said release mechanism releases said selected fragrance at a higher rate than in said second state.

The fragrance delivery system according to the present invention has the advantage that the fragrance may be delivered at a desired intensity, taking the size of the space to which the fragrance needs to be delivered into account.

Suitably, said selection unit is arranged to periodically select, in response to a selection signal, instead of a presently selected fragrance another selected fragrance, which delivery system further comprises a timer for measuring a period of time during which said presently selected fragrance has been released, and a comparator for comparing said measured period with a predetermined value representing a desired period and outputting said selection signal to the selection unit.

In this way a sequence of selected fragrances can be released. In accordance with the present invention at least one fragrance can be selected from at least two fragrances. Preferably, one fragrance is selected from at least two fragrances. More preferably, one fragrance is selected from three fragrances.

Suitably, the present delivery system a further comprises a timer for measuring a period of time of said first state and/or second state, a memory element in which at least one desired value of a period of the first and/or second state can be stored, and a comparator for comparing the measured period with said desired value and outputting a switching signal to said switching element, and wherein said switching element is arranged to change said state in response to said switching signal.

Suitably, said switching element is arranged to switch said release mechanism between said first state and said second state during a first period of time, and to switch said release mechanism between said first state and said second state during a second period of time, in which second period of time the ratio of the duration of the first state relative to the duration of the second state is lower than in the first period of time.

Suitable values for the combined first and second period are found to be in the range of 15 to 60 minutes. The first period has suitably a longer duration than said second period. For example, the first period may have a duration of more than 15 minutes, such as between 20 and 60 minutes, and/or in less than or equal to 60 minutes. The second period may for example have a duration of less than 30 minutes, such as between 10 and 25 minutes.

Suitably, the selected fragrance can be released during both the first period of time and the second period of time in a continuous manner. When a lower overall fragrance intensity is required, each of the selected fragrances can suitably be released in a series of first stages and second states, in the form of pulses. Hence, the first state will be switched to the second state, after which the second state can be switched to the first state. The period of time in which such a series of the first states and the second states can be switched from one to the other is suitably in the range of from 15 to 60 minutes, preferably in the range of from 20 to 40 minutes, more preferably in the range of from 25 to 35 minutes. During such a period of time the duration of the first states is preferably in the range of from 100 to 200 seconds, and the duration of the second states is preferably in the range of from 20 to 100 seconds.

Suitably, the release mechanism can be disconnected or switched off after each first state to ensure that less fragrance will be released during each second state.

The last first state in such a series of first and second states can be followed up with a single second state of which the duration is preferably in the range of from 5 to 30 minutes, more preferably in the range of from 10 to 20 minutes. During such a single second state the release of the selected fragrance will be less than the release during the preceding first state. Suitably, said release mechanism can be disconnected or switched off to ensure that less or no fragrance will be released during such a single second state. Such a single second state can suitably be followed up with a single first state of another selected fragrance or a series of first states and second states of another selected fragrance. Such a single first state or the last first state in a series of first and second states of the other fragrance can in turn be followed by another single second state, after which a single first state or a series of first and second states can be applied of yet another selected fragrance.

The duration of the first and second states can suitably be adjusted so as to bring about an overall fragrance intensity which is appropriate for the space into which the fragrances(s) is (are) released. The overall fragrance intensity will become higher when the duration of the first states becomes longer, whereas it will decrease when the duration of the second state(s) become(s) longer.

Suitably, the duration of the respective first and second states during the period that a particular fragrance is released can be varied. Suitably, at least two sets of desired values of the durations of the first and second state(s) are provide, preferably three sets of desired values of the durations of the first and second state(s). In one such a set the duration of the first states in a series of first and second states may be 200 seconds and the duration of the second states may be 40 seconds, whereas in another set the duration of the first states may be 150 seconds and the duration of the second states may be 100 seconds. It will be understood that the overall fragrance intensity as experienced by an individual will be higher with the former set than with the latter set. Thus, the present invention provides flexibility to ensure that the overall fragrance intensity as experienced by an individual can be adjusted to meet appropriately the size of the space to which the fragrance(s) is (are) released.

Suitably, the fragrance delivery system has three modes of operation, namely two modes of operation which provide lower overall fragrance intensities in which each mode use is made of a different set of desired values of the duration of the series of first and second states, whereas in a third mode of operation in the first period and second period of time the fragrance is released continuously, without pulses, providing a maximum overall fragrance intensity.

Suitably, said first period has a longer duration than said second period.

During the second period of time, said release mechanism is suitably in the second state only.

Preferably, said first period and said second period follow in an alternating manner.

Suitably, in the second state said release mechanism releases said selected fragrance at a rate below a threshold at which an individual notices said fragrance, such as a rate of substantially zero.

Preferably, said selection unit is arranged to periodically select a selected fragrance.

Preferably, said selection unit is arranged to select a selected fragrance when a second period expires.

Suitably, said release mechanism includes an electro-thermal transducer, said transducer being electrically connectable to a electrical power source and which transducer can be coupled thermally to a fragrance substance, for converting electrical energy from said power source to thermal energy applied to said selected fragrance.

The present delivery system suitably further comprising a holder for holding at least two fragrance containers.

Suitably, a release mechanism engageable on said fragrance containers, for releasing a selected one of at least two fragrances from said fragrance container.

The timer is capable of measuring a first period of time in the range of from 100 to 200 seconds, and a second period of time in the range of from 20 to 100 seconds.

Suitably, the fragrance delivery system further comprising a release mechanism for releasing a selected one of at least two fragrances from said fragrance container. Preferably, the release mechanism comprises a heater which allows the fragrance to be released from the container at a particular temperature.

Suitably, the heater will be heated to the active state enabling the fragrance to vaporize, whereas the heater will be switched off during the inactive state.

The heater can be of any form, for instance, in the form of a ring or a coil around the wick means of the container containing the fragrance substance.

The selection unit is arranged in such a way that the at least two fragrances are selected in an alternating manner.

Such release mechanism can either be part of the holder for holding the at least two fragrance containers or at may be part of each of the fragrance containers. Accordingly, the at least two fragrance containers can suitably each be provided with a release mechanism to release the fragrance contained in the fragrance container.

Preferably, the fragrance delivery system according to the present invention is capable of releasing at least three different fragrances in an alternating manner.

The fragrance substance can suitably be in the form of a liquid, gel or solid. The fragrance substance is preferably in the form of a liquid. Suitable solvents for the fragrance substances include those known in the art such as water, propanol, ethanol and appropriate ethers, carbitols and glycols.

Preferably, the fragrance delivery system according to the present invention is adapted to be connected to an electric power supply, for instance, a domestic main socket, to allow the control unit and switching element to function.

These and other aspects of the invention will be apparent from and elucidated with reference to the embodiments described hereinafter. Specific embodiments of the invention are set forth in the dependent claims. Further details, aspects and embodiments of the invention will be described, by way of example only, with reference to the attached drawings.

DETAILED DESCRIPTION OF EXEMPLARY EMBODIMENTS

Figure 1:
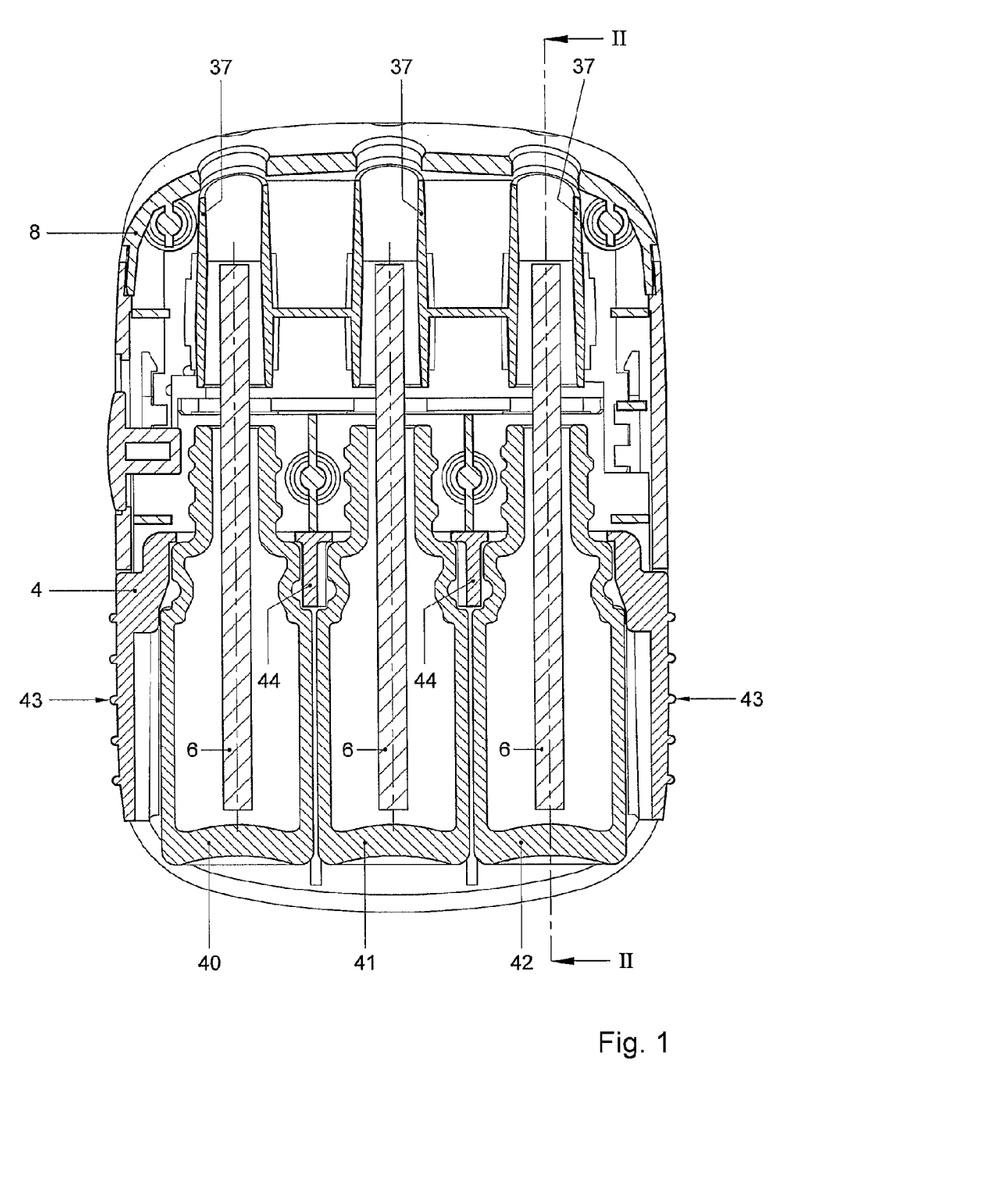
FIG. 1 schematically shows a cross-sectional view of an example of an embodiment of a fragrance delivery device according to present invention.
Figure 2:
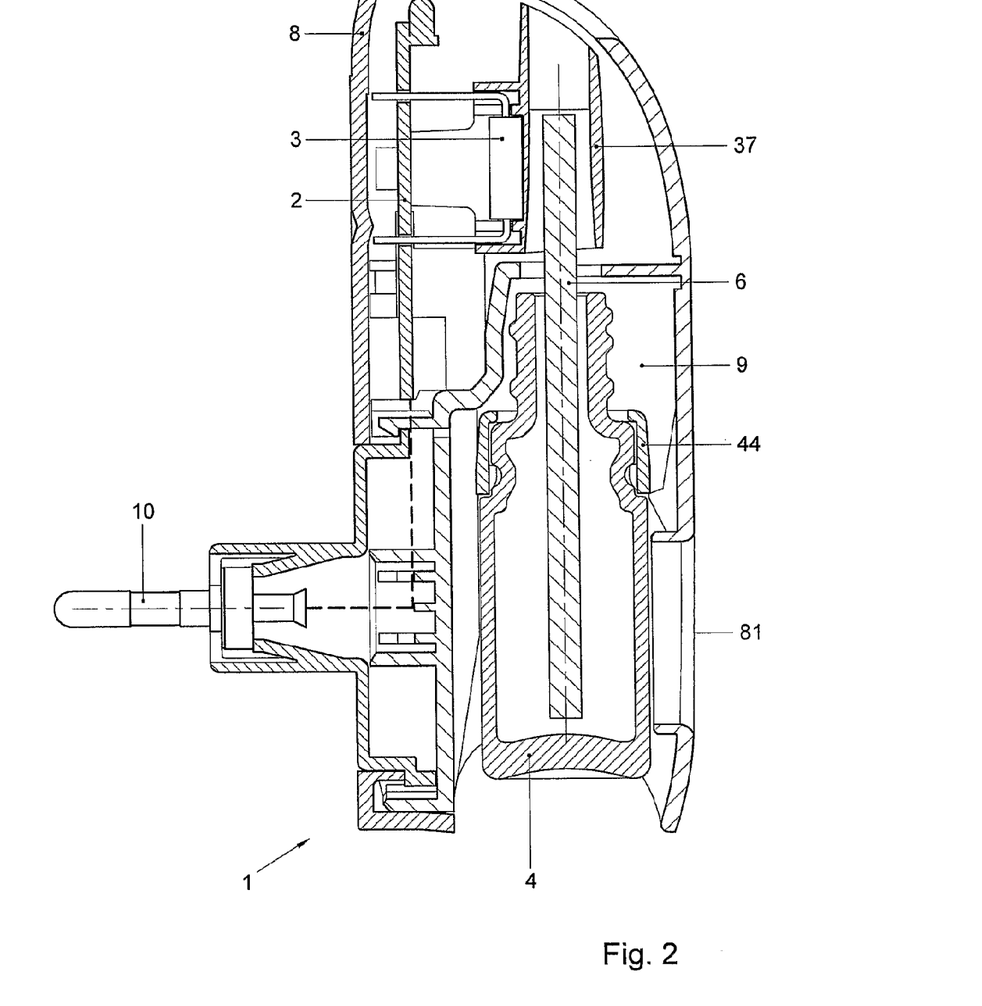
FIG. 2 schematically shows a cross-sectional view of the example of FIG. 1 along the line II-II.

The example of a fragrance delivery system 1 shown in FIGS. 1 and 2 comprises a control unit 2 and a release mechanism 3. The control unit 2 is connected to the release mechanism 3. The release mechanism 3 can, as is explained below in more detail, release one or more selected fragrances. The control unit 2 can control via a suitable control signal which fragrance is selected and released by the release mechanism.

In the example of FIGS. 1 and 2 the release mechanism 3 can operate on one or more fragrance reservoirs 40-42 to release one or more selected fragrances from a number of fragrances present in the fragrance delivery system 1. In this example, the release mechanism 3 comprises a number of heating elements 30-32, as is shown more clearly in FIGS. 3 and 4. Each of the heating elements 30-32 is in thermal contacts with at least a part of the fragrance chemical in a different one of the fragrance reservoirs 40-42. The heating elements 30-32 may be controlled separately by the control unit 2 to heat the selected fragrance chemical. This heating causes an increased release, e.g. by evaporation or sublimation of the fragrance substance from the respective reservoir 40-42.

Figure 3:
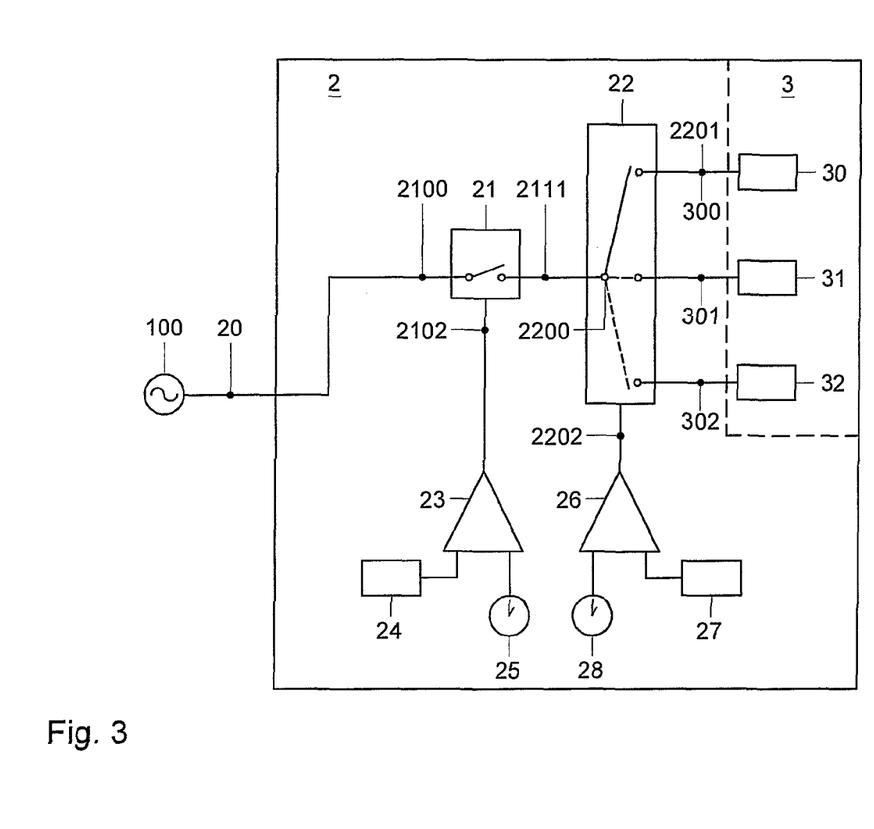
FIG. 3 schematically shows a block diagram of a first example of an embodiment of a control unit suitable for the example of FIGS. 1 and 2.
Figure 4:
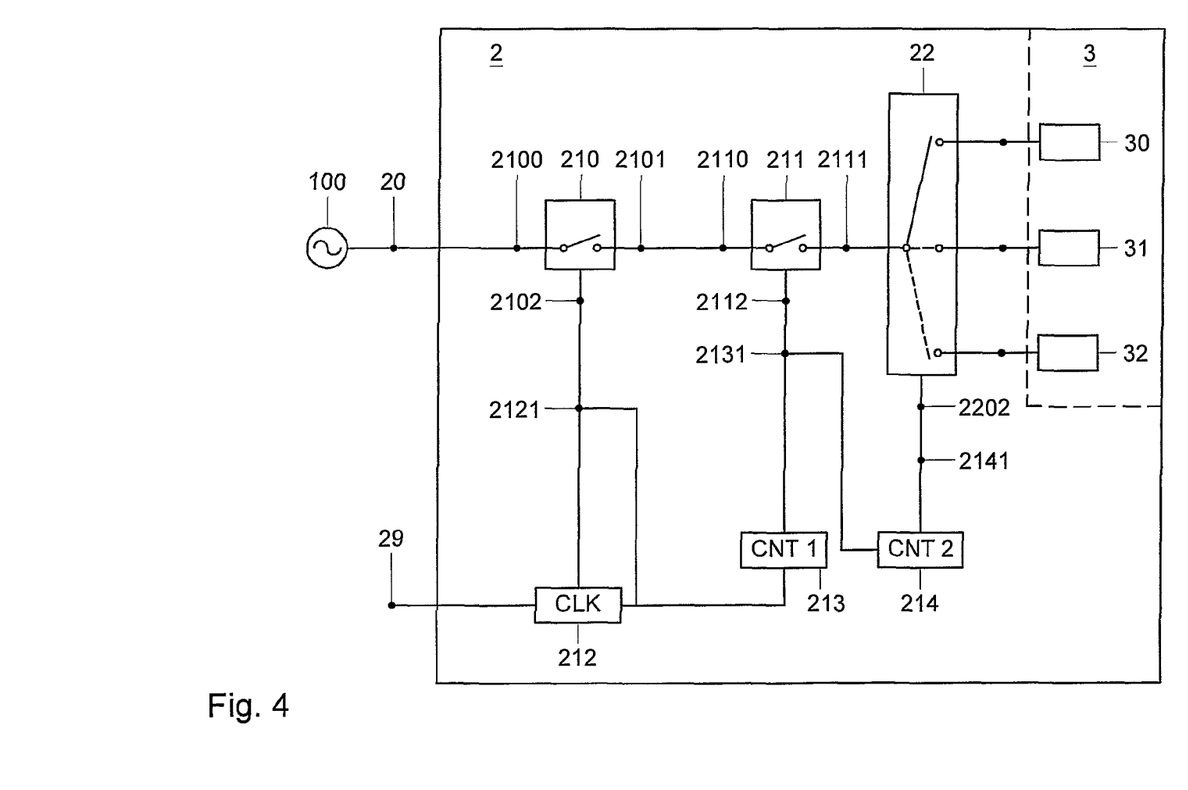
FIG. 4 schematically shows a block diagram of a second example of an embodiment of a control unit suitable for the example of FIGS. 1 and 2.

The heating element 30-32 may be implemented in any manner suitable for the specific implementation. The heating element may for example be implemented as a resistor or other electro-thermal transducer which can convert electrical energy into thermal energy and supply the thermal energy to the fragrance substance.

The control unit 2 is arranged to select a heating element 30-32 which can heat the selected fragrance. FIG. 3 shows a block diagram of an example of the control unit 2. The example of FIG. 2 comprises a selection unit 22 for selecting the selected fragrance from the fragrances present in the fragrance delivery system 1. E.g. in this example, the selection unit 22 has an input and a plurality of outputs. Each of the outputs is connected to an input 300-302 of another heating element 30-32. The selection unit 22 provides an electrical connection between the input and a selected one of the outputs. Via the selection unit 22 energy, e.g. in this example electrical power, is provided to the selected output and hence to a selected heating element 30-32. Via the heating element the provided energy is used to release the selected fragrance. Accordingly, by controlling the selected output of the selection device 22, the fragrance being released may be selected.

In the examples of FIGS. 3 and 4, the control unit 22 can control the release mechanism 3 to be in a first state or in a second state. In the first state the selected fragrance is released at a higher rate than in the second rate. It is found that by varying the rate, the habituation to the fragrance may be reduced. For example, by varying the rate between a first state in which the rate lies above a threshold at which an individual notices said fragrance and a second state in which the rate lies below this threshold, habituation is found be reduced substantially. In the second state, the rate may for example be very low or even zero, thus prolonging the period a reservoir may be used without requiring refills.

In the example of FIG. 3 for instance, the control unit 2 comprises a switching element 21 which in a conducting state allows a current flow between a switch input 2100 and a switch output 2111, whereas in a non-conducting state the current flow between the switch input 2100 and the switch output 2111 is inhibited, or at least less than in the conducting state. Thus, depending on the state of the switch more or less current flows to the selected heating element 30 and accordingly more or less thermal energy is provided to the selected fragrance and accordingly the release rate of the selected fragrance is varied.

The state of the switching element 21 may be controlled by a switch control signal provided at a switch control input 2102. In the example of FIG. 3, the switch control signal is generated by a switch control circuit. The switch control circuit comprises a timer 25 which measures the duration of the state of the switch. The switch control circuit further comprises a memory 24 in which a desired value of the duration of the conducting and/or non-conducting state is stored. A comparator 23 is connected to the memory 24 and the timer 25 and can compare the measured duration with the value stored in the memory 24. When this comparison reveals that the measured period is below the stored value, the comparator outputs a first signal to the switch control input 2102 in response to which the switch is e.g. in the conducting state and when this comparison reveals that the measured period is above the stored value, the comparator outputs a second signal to the switch control input 2102 in response to which the switch is e.g. in the non-conducting state. Thus, the state of the switch and accordingly the state of the selected heating element 30-32 may be controlled.

Figure 5:
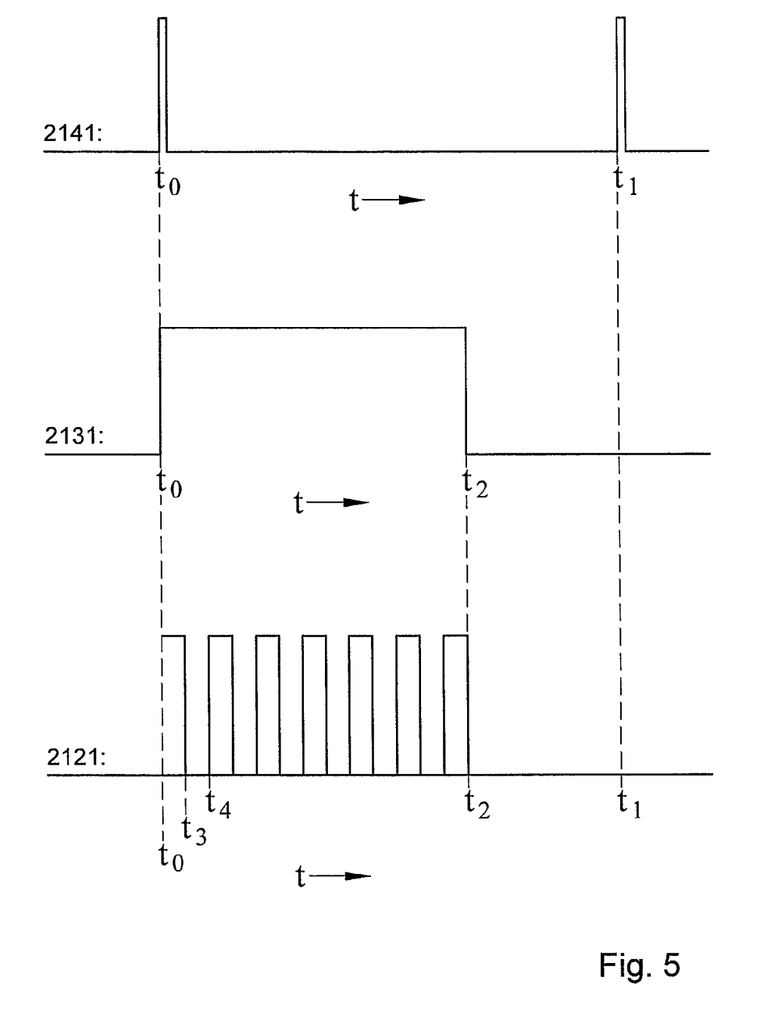
FIG. 5 shows a timing diagram of outputs in example of FIG. 4.

In the example of FIG. 4, the switching element 21 is arranged to switch the release mechanism 3 between the first state and the second state during a first period of time, e.g. between $t_0$ and $t_2$ in the timing diagram of FIG. 5. Thereby, the fragrance intensity may be adjusted during the first period to meet more appropriately the size of the space to which the fragrance is to be delivered. For example, by controlling e.g. the duty cycle of the switching between the first state and the second state, the average release rate during the first period may be controlled. Thus, for example, the release rate of the selected fragrance may be adapted to a room in which the fragrance delivery system 1 is provided in a simple manner and the need for complex control elements which for example control the temperature to which the fragrance chemical is heated is obviated. The control of the first state and the second state may be implemented in any manner suitable for the specific implementation. In the example of FIG. 4, for instance, the control circuit has a release control input 29 by means of which the duty cycle of the signal generated by the clock 212 may be controlled. for example manually.

During the first period, the release mechanism 3 may be switched between the first state and the second state in an alternating manner. A cycle of the first state and second state may have any period suitable for the specific implementation. For example, the duration of the first state may be in the range of from 100 to 200 seconds, and the duration of the second state may be in the range of from 20 to 100 seconds. The ratio of the duration of the first state relative to the duration of the second state may have any value suitable for the specific implementation and for example be in the range of 2 to 5 during the first period.

The switching element 21 may further be arranged to switched the release mechanism 3 between the first state and the second state in a different manner during a second period, e.g. between $t_2$ and $t_1$. In the example o FIG. 4, during the second period of time for instance, the ratio of the duration of the first state relative to the duration of the second state may lower than in the first period of time. For instance, as shown in FIG. 5 during the second period the first state may be absent, e.g. the ratio is (almost) zero. In FIG. 5, the output signals of the counter 214 (at output 2141), the counter 213 (at output 2131), and the selection unit 22 (at output 2202) are shown respectively as a function of time t.

In the example of FIG. 4, for instance, the switching element 21 comprises a first switch 210 which is alternately switched between a conducting state and a non-conducting state with a switching period T much shorter than the first period. The state of the first switch 210 is controlled by a suitable control signal provided to a control input 2102 of the switch 210 by a clock 212.

The switching element 21 further has a second switch 211 which is alternately switched between a conducting state and a non-conducting state by a control signal provided at a control input 2112. The control signal is presented to the control input 2112 at a counter output 2131 of a counter 213. An input of the counter 213 is connected to the output 2121 of the clock 212. The counter 213 controls the second switch 211 to be in the conducting state during a period of time corresponding to the first period and in the non-conducting state during a period of time corresponding to the second period. The counter 213 may for example count the number of periods of the clock signal and switch the second switch to the non-conducting state or vice versa after a number of periods corresponding to the duration of the first period. In During the second period of time, the release mechanism may for instance be in the second state only. In the example of FIG. 4, the second switch 211 inhibits a current to the release mechanism 3 during the entire second period and hence controls the release mechanism to be in the second state with a release rate of substantially zero.

Preferably, the second period is sufficiently long to reduce the detection level of a human being, such as to the level before habituation, whereas the first period may be sufficiently short to prevent rising the detection level above the concentration of the selected fragrance in the space in which the fragrance delivery system 1 is positioned. Suitable values for the combined first and second period are found to be in the range of 15 to 60 minutes. The first period has suitably a longer duration than said second period. For example, the first period may have a duration of more than 15 minutes, such as between 20 and 60 minutes, and/or in less than or equal to 60 minutes. The second period may for example have a duration of less than 30 minutes, such as between 10 and 25 minutes.

The first period and said second period may for example follow in an alternating manner. For example, a number of cycles of alternating the first period and the second period may be performed. The duration of the first period and/or second period may differ per cycle or be constant in time.

In the example of FIGS. 3 and 4, the selection unit is arranged to periodically select a selected fragrance. In the example of FIG. 3, to that end the selection unit has a control input 2202 which is connected to an output of a comparator 26. The comparator 26 has an input which is connected to a memory 27 and another input is connected to a timer 28. In the memory 27 a desired value of a period of time during which a fragrance is selected may be stored and by means of the comparator 26 a duration measured by the timer 28 may be determined. In case the measured duration exceeds the desired value, the selection unit 22 is controlled by the comparator 26 to select another fragrance. In this respect, the comparator may select a fragrance which is not presently selected or select the presently selected fragrance again.

The selection unit 22 may be arranged to select the fragrances in a predetermined order. In such case, for example, the fragrances may be selected to generate a certain atmosphere or user experience. However, it is also possible to select the fragrances at random, thereby further reducing the habituation of an individual to the fragrances.

The selection unit 22 may for instance be arranged to select a selected fragrance when a second period expires. In the example of FIG. 4, for example, a control input 2202 of the selecting unit 214 is connected to an output 2141 of a counter 214. The counter 214 counts the periods of the signal outputted by the counter 213 connected the second switch 211. In case the output signal of the counter 213 has completed one cycle of a first period and a second period, the counter outputs, as shown in FIG. 5, a control signal to the selection unit 22 in response to which the selection unit 22 selects a heating element 30-32 to provide a current and hence selects a fragrance.

The selection unit may be arranged to select randomly the selected fragrance from the at least two fragrances in case the delivery system 1 is turned on. Thereby the different fragrances are used more and the change that one reservoir is empty before the other reservoirs is reduced.

Returning to FIGS. 1 and 2, the control unit 2 is provided in a housing 8. The control unit 2 may be connected by means of a plug 10 to a conventional (not shown) socket and hence to a power source 100.

In the example of FIGS. 1 and 2, the release mechanism 3 further comprises a wick 6 which can transport the fragrance out of the reservoir 40-42 into the vicinity of a respective heating element 30-32. The wick 6 may be made of natural or synthetic fibrous materials such as fibreglass, cotton, graphite, mineral fibres, and polyester. The wick extends into a passage 37, which may also be referred to as a chimney. The heating element 30-32 is provided on the outside of the passage 37 and in thermal contact with the inside thereof. The heating element 30-32 may be of any form, for instance, in the form of a ring or a coil around the wick means. Thermal energy is transported from the heating element to the inside of the passage 37 via the passage wall. The thermal energy in the inside of the passage 37 heats the fragrance transported by the wick 6 and thus volatilizes the fragrance. The volatilized fragrance may subsequently be released out of the fragrance delivery system via an open side at the top of the passage 37

It should be noted that the release mechanism 3 may also be implemented in a different manner and for example comprise a pressurizing means which provides a pressure into a reservoir and thereby pumps the fragrance out of the reservoir via a vent.

The fragrance chemical may be of any type suitable for the specific implementation. In case the release mechanism heats the fragrance substance, the fragrance substance may for instance be of a type with a low release at room temperature and exhibit an increased evaporation or sublimation at elevated temperatures (i.e. above room temperature). Such a fragrance substance may be volatilized by increasing the temperature above room temperature, such as to 60° Celsius of higher, such as to 70° Celsius or higher, such as to 75° Celsius or higher, 80° Celsius or higher for example. The fragrance may be provided in the reservoirs 40-42 in any phase. The reservoirs 40-42 for may for example be contain a fluid which comprises the fragrance substance. The fragrance substance can be in the form of a liquid, gel or solid. The fragrance substance is preferably in the form of a liquid. Suitable solvents for the fragrance substances comprise those known in the art such as water, propanol, ethanol and appropriate ethers, carbitols and glycols.

In the example of FIGS. 1 and 2, the fragrance delivery system further comprises a holder 9 for holding the two fragrance reservoirs 40-42. In the example, the holder 9 comprises a recess in the housing 8 in which the fragrance reservoirs 40-42 may be placed and be fixated in position relative to the housing 8. When one or more of the fragrance reservoirs 40-42 are empty or when replacing or removing the fragrance reservoirs is desired for other reasons, the fragrance reservoirs 40-42 may be released from the fixated position, in this example manually by pressing clamp constructions 43 which engage on the fragrance reservoirs to lock the fragrance reservoirs 40-42 in position.

Figure 6:
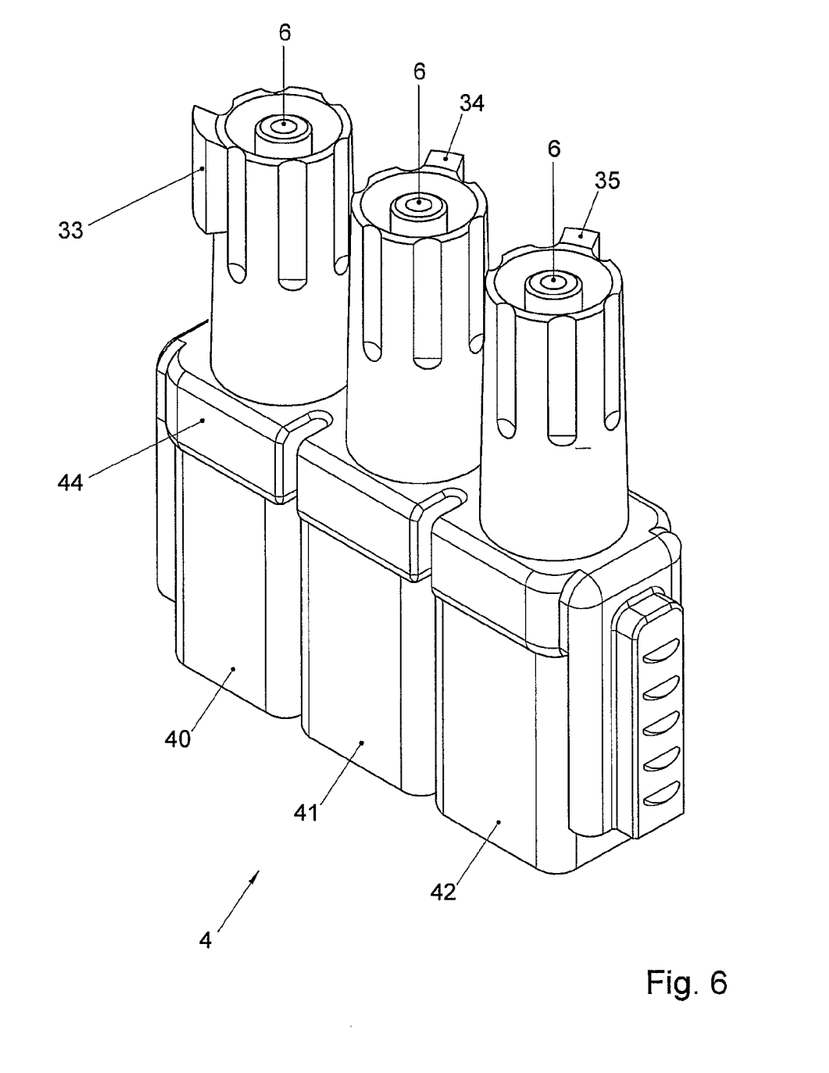
FIG. 6 schematically shows a perspective view of an example of an embodiment of a cartridge suitable for the example of FIGS. 1 and 2.

In the example of FIGS. 1 and 2, the release mechanism 3 is incorporated in the housing 8. In case one or more reservoirs are removed from the housing, the release mechanism is not removed. Accordingly, the construction of the reservoirs is more simple. However, as shown in FIG. 6, at least a part of the release mechanism may be provided on the reservoirs 40-42. in the example of FIG. 6, heating elements 33-36 in the form of resistors are placed on the outside of the reservoirs 40-42. When the reservoirs 40-42 are placed in the housing 8, the heating elements 33-36 are electrically connected to the control unit 2 and the power source, for example by exposed metal contacts in the housing and on the heating elements.

Preferably, the fragrance delivery system according to the present invention is adapted to be connected to an electric power supply, for instance, a domestic main socket, to allow the control unit and switching element to function.

The at least two fragrances may differ from each other completely or they may be related to each other. It will be understood that each fragrance may be composed of a number of fragrance components. Suitably, the at least two fragrances are related to each other. For instance, a first fragrance may be associated with oriental bamboo, whereas a second fragrance associated with relaxing incense. The fragrances to be used may be selected from a group of types of scents. The fragrances can, for instance, share a common theme. In a very attractive embodiment of the present invention the fragrances complement each other. In the context of the present invention the term "complement" means that the fragrances used convey to a particular theme in the sense that it provides a special physiological effect. The themes can relate to various times of the day, particular geographical regions such as the Orient, seasons of the year, and particular aromas such as vanilla-related fragrances. Suitable themes comprise, for instance, "Oriental Dreams" which an individual will associate with tropical fragrances, "Heavenly Flowers" which an individual will associate with floral fragrances, and "Seaside Stroll" which an individual will associate with fragrances experienced at the seashore.

The present invention also relates to a kit of parts comprising the fragrance delivery system according to the present invention and at least two fragrance reservoirs filled with a fragrance chemical. As shown in the example of FIGS. 1 and 2 and of FIG. 6, the fragrance reservoirs can be part of a fragrance cartridge 4. In these example the cartridge 4 includes a carrier 44 which fixates a number of fragrance reservoirs 40-42 to each other.

The bottles may for example be made of glass or a plastic material. In the example of FIGS. 1 and 2, the fragrance reservoirs are formed as bottles of an optically transparent material. The housing 8 is provided with one or more windows 81 via which the content of the bottles may be viewed.

The present invention further relates to the use of a control unit for controlling a release mechanism to release a selected one of at least two fragrances in a fragrance delivery system, which control unit comprises a selection unit for selecting said selected fragrance and controlling said release mechanism to release said selected fragrance, and a switching element for switching said release mechanism between an active state and an inactive state or vice versa.

In addition, the present invention relates to the use of the fragrance delivery system according to the present invention or the kit of parts according to the present invention to deliver a fragrance to a space which is at least periodically occupied by an individual.

In the foregoing specification, the invention has been described with reference to specific examples of embodiments of the invention. It will, however, be evident that various modifications and changes may be made therein without departing from the broader spirit and scope of the invention as set forth in the appended claims. For example, the switches shown in the examples may be implemented as transistors or other suitable electronic components. Also, the fragrance delivery system may be capable of releasing at least three different fragrances in an alternating manner and include a housing which is adapted to hold three different reservoirs.

Furthermore, the control unit may be implemented in non-programmable hardware or as one or more programmable devices or units able to perform the desired device functions by operating in accordance with suitable program code. Furthermore, the devices may be physically distributed over a number of apparatuses, while functionally operating as a single device. For example, the control unit may be implemented as a circuit of discrete electronic components. Also, devices functionally forming separate devices may be integrated in a single physical device. For example, the control unit may be implemented as a single integrated circuit.

In the claims, any reference signs placed between parentheses shall not be construed as limiting the claim. The word 'comprising' does not exclude the presence of other elements or steps then those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to advantage.

The invention claimed is:

1. A fragrance delivery system, comprising:
a control unit configured to control a release mechanism to release at least one selected fragrance, said control unit comprising a selection unit configured to select said selected fragrance from at least two fragrances and said control unit controlling said release mechanism to release said selected fragrance, and
a switching element configured to switch said release mechanism between a first release state and a second release state or vice versa,
wherein said release mechanism releases said selected fragrance from said fragrance delivery system to a space in said first release state and in said second release state, and wherein said release mechanism releases said selected fragrance at a higher rate in said first release state than in said second release state, and
wherein said switching element is further configured to switch said release mechanism between said first release state and said release second state during a first period of time, and to switch said release mechanism between said first release state and said second release state during a second period of time, wherein said first period of time is longer in duration than said second period of time,
a timer configured to measure a measured period of said first state in the range of from 100 to 200 seconds and a measured period of said second state is in the range of from 20 to 100 seconds,
a memory element in which at least one desired value of a period of the first and/or second state may be stored, and
a comparator configured to compare said measured period of said first and/or second state with said desired value and output a switching signal to said switching element,
wherein said switching element is arranged to change said release mechanism between said first state and said second state in response to said switching signal.

2. The fragrance delivery system according to claim 1, wherein in the second period of time the ratio of the duration of the first state relative to the duration of the second state is lower than in the first period of time.

3. The fragrance delivery system according to claim 2, wherein said release mechanism comprises a heating element wherein, during the second period of time, said heating element is configured to release said selected fragrance in the second state only.

4. The fragrance delivery system according to claim 1, wherein said release mechanism comprises an electro-thermal transducer, said transducer being electrically connectable to an electrical power source configured to be coupled thermally to a fragrance chemical, the transducer further configured to convert electrical energy from said power source to thermal energy applied to said selected fragrance.

5. The fragrance delivery system according to claim 1, further comprising a holder for holding at least two fragrance reservoirs.

6. The fragrance delivery system according to claim 5, wherein said release mechanism comprises a heating element in thermal contact with at least a part of a fragrance chemical in said fragrance reservoirs and is configured to release a selected one of at least two fragrances from said fragrance reservoirs.

7. A kit of parts comprising a fragrance delivery system according to claim 1 and at least two fragrance reservoirs filled with a fragrance chemical.

8. The kit of parts according to claim 7, wherein the release mechanism comprises a release mechanism provided for each of the at least two fragrance reservoirs configured to release the fragrance chemical contained in each of the at least two fragrance reservoirs.

9. The kit of parts according to claim 7, wherein the at least two fragrance reservoirs are part of a fragrance cartridge.

10. The kit of parts according to claim 7, wherein the fragrance chemical in each of the at least two fragrance reservoirs are different and complement each other.

11. A method comprising the use of a fragrance delivery system according to claim 1 to deliver a fragrance to a space which is at least periodically occupied by an individual.

\* \* \* \* \*